United States Patent
Peters et al.

(10) Patent No.: US 8,328,750 B2
(45) Date of Patent: Dec. 11, 2012

(54) REMOVABLE MULTIPLE PANEL ASSEMBLY WITH BLOOD SUPPLY AND FLUID TUBING FOR HEMOFILTRATION APPARATUS

(75) Inventors: Harold Peters, Snow Hill, NC (US); Adam Heintzelman, Oakland, CA (US); Jacob Kearns, El Sobrante, CA (US); Tommy Cooper, Friendswood, TX (US)

(73) Assignee: B. Braun Avitum AG, Melsungen (DE)

( * ) Notice: Subject to any disclaimer, the term of this patent is extended or adjusted under 35 U.S.C. 154(b) by 636 days.

(21) Appl. No.: 12/577,578

(22) Filed: Oct. 12, 2009

(65) Prior Publication Data
US 2010/0094192 A1  Apr. 15, 2010

Related U.S. Application Data

(60) Provisional application No. 61/105,703, filed on Oct. 15, 2008.

(51) Int. Cl.
*A61M 37/00* (2006.01)
(52) U.S. Cl. ........................ 604/6.06; 210/646
(58) Field of Classification Search ................. 604/5.01, 604/5.04, 6.06, 6.07, 6.09, 6.11; 210/645, 210/646
See application file for complete search history.

(56) References Cited

U.S. PATENT DOCUMENTS

| | | | |
|---|---|---|---|
| 5,200,090 | A | 4/1993 | Ford et al. |
| 5,605,627 | A | 2/1997 | Carlsen et al. |
| 5,679,245 | A | 10/1997 | Manica |
| 5,910,252 | A | 6/1999 | Truitt et al. |
| 6,200,485 | B1 | 3/2001 | Kitaevich et al. |
| 6,659,973 | B2 | 12/2003 | Gorsuch et al. |
| 6,849,183 | B2 | 2/2005 | Gorsuch et al. |
| 7,232,418 | B2 | 6/2007 | Neri et al. |
| 7,247,146 | B2 | 7/2007 | Tonelli et al. |
| 2009/0084717 | A1 | 4/2009 | Delmage et al. |
| 2010/0089806 | A1 | 4/2010 | Peters et al. |
| 2010/0094194 | A1 | 4/2010 | Peters et al. |

OTHER PUBLICATIONS

Sueoka, A., "Present Status of Apheresis Technologies: Part 2. Membrane Plasma Fractionator", vol. 1, No. 2, May 1997, pp. 135-146.

*Primary Examiner* — Melanie Hand
(74) *Attorney, Agent, or Firm* — RatnerPrestia

(57) ABSTRACT

A panel assembly for being manually mounted on a blood therapy apparatus is characterized by three panels, a center panel configured for manually securing a hemofilter cartridge and opposite side panels, hingedly connected to the center panel. The side panels have generally flat, planar interior surfaces defined by a rim extending around its perimeter. Tubing is secured along and adjacent to the interior panel surfaces, which are also provided with tubing supports having slanted tubing channels for supporting arched pump rotor engaging tubing sections and prevent tubing droop.

42 Claims, 5 Drawing Sheets

REMOVABLE MULTIPLE PANEL ASSEMBLY WITH BLOOD SUPPLY AND FLUID TUBING FOR HEMOFILTRATION APPARATUS

CROSS REFERENCE TO RELATED APPLICATIONS

This application claims priority to U.S. Provisional Patent Application No. 61/105,703 filed Oct. 15, 2008 and is incorporated herein by reference.

BACKGROUND OF THE INVENTION

In co-pending U.S. patent application Ser. No. 12/183,527 filed Jul. 31, 2008 (TRANSVI.024A), incorporated herein by reference in its entirety, there is described a modular hemofiltration apparatus with removable panels provided with tubing sets mounted on the panels and configured for easy manual installation and replacement on a modular hemofiltration apparatus housing. The present application describes in more specific and complete detail preferred embodiments of a multiple panel assembly and tubing components as well as panel features for improved and efficient setup, operational flexibility and performance.

SUMMARY OF THE INVENTION

Described herein is a panel assembly comprising a first panel having blood supply tubing secured along the interior panel surface and a blood support tubing member with slanted tubing support channels, the support member formed on and protruding from the interior panel surface and a plurality of pressure transducers mounted on the interior panel surface, a second panel having fluid supply tubing secured along the interior panel surface and a plurality of fluid tubing support members with slanted tubing support channels, the support members formed on and protruding from the interior panel surface, and a third panel positioned between the first and second panels, flexibly connected to both panels and configured to support a blood filter cartridge. The blood supply tubing comprises blood inlet tubing segments, a first blood inlet tubing segment mounted in the tubing support channels of the blood tube support member and having an arched tubing section configured for engaging a blood pump rotor. The fluid supply tubing comprises first, second and third fluid tubing segments each having an arched tubing section mounted on different ones of the tubing support members and configured for engaging fluid pump rotors. The tubing support channels are slanted upwardly in the direction of the curve of the arched tubing sections to prevent tubing droop and thereby improve tubing configuration for engaging pump rotors. The second panel is also provided with a fluid tubing bridge formed on and projecting from the interior panel surface and configured for supporting a length of fluid tubing for engagement with a blood detector in a substantially vertical axial orientation. The aforesaid assembly, components and configurations thereof will be more fully explained in the following detailed description.

DETAILED DESCRIPTION OF EMBODIMENTS

Figure 1:
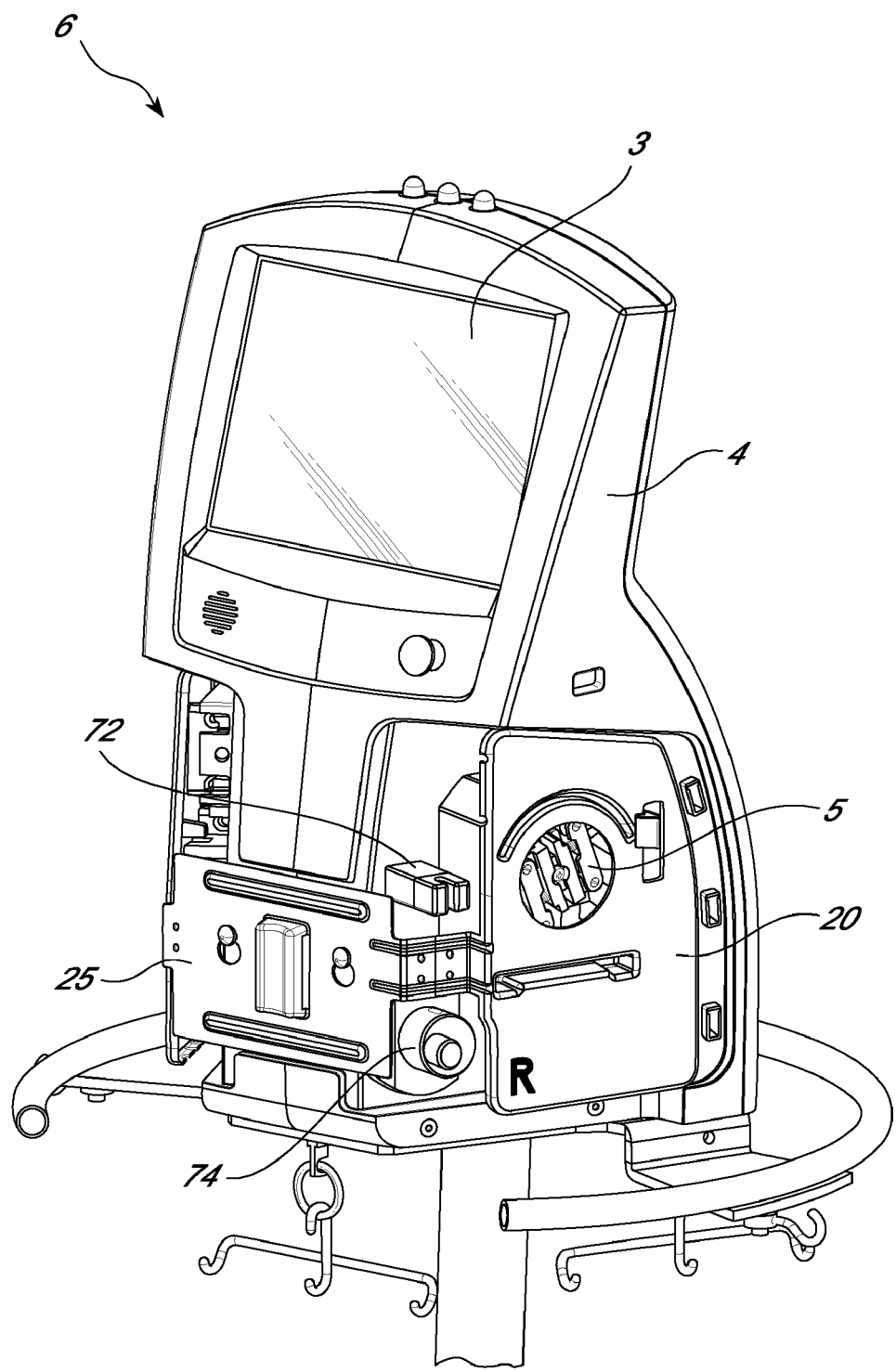
FIG. 1 is a perspective view of the hemofiltration control apparatus showing front and one side of the panel assembly mounted on the control unit housing.
Figure 2:
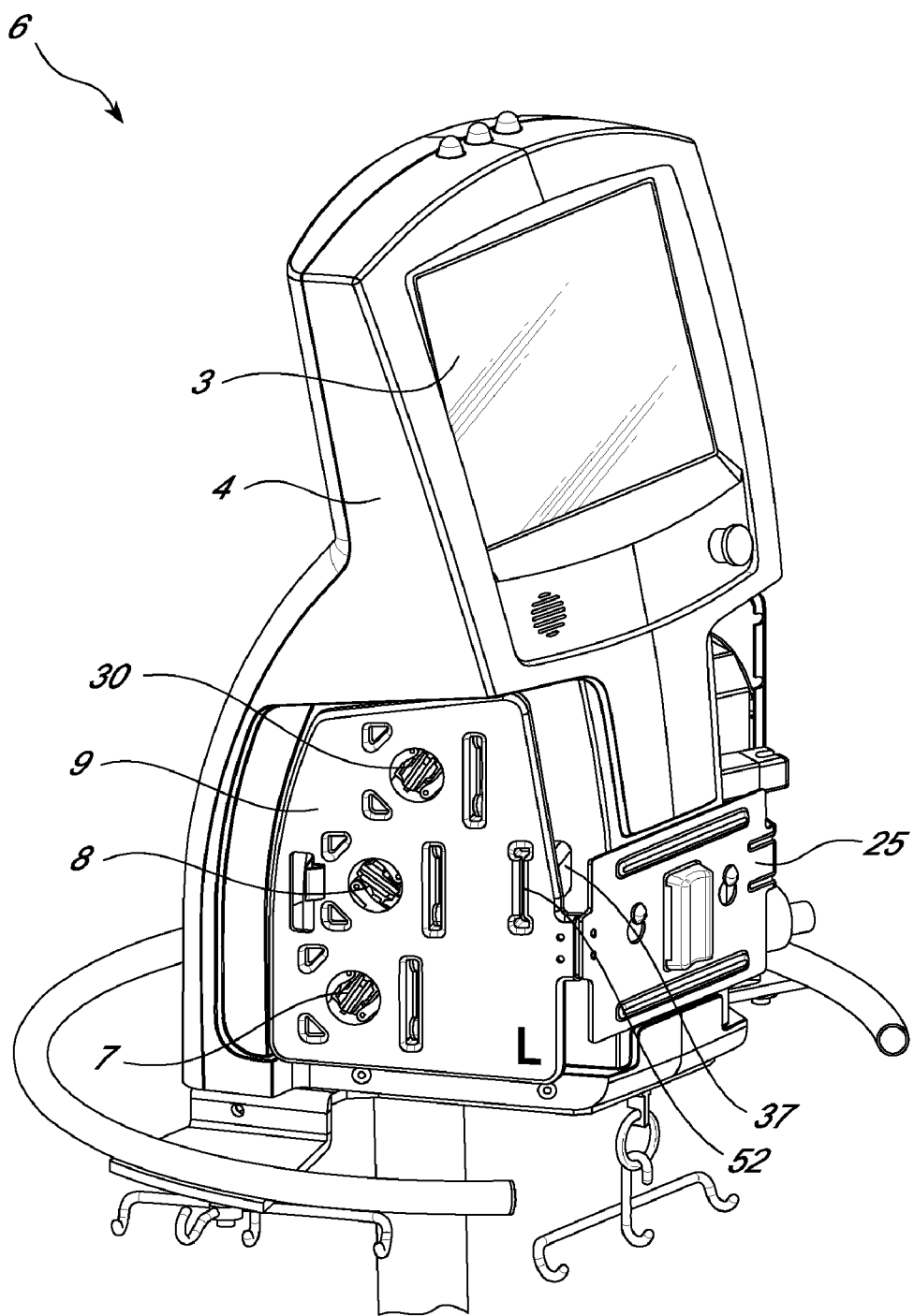
FIG. 2 is a perspective view showing the other side and front of the mounted panel assembly.

FIGS. 1 and 2 show the hemofiltration assembly 6, illustrating opposite side views from the front corners of the apparatus, respectively. In FIG. 1, the blood side is shown with the rotor 5 of the blood pump viewable through an opening in blood panel 20, and on the other side three fluid pump rotors 7, 8, 9 are visible through viewing ports in fluid control panel 30. Front or third panel 25 is seen in both figures, as is a touch-screen 3. All three panels of the panel assembly are mounted on the housing or case 4 as will be explained further hereinafter, as well as in U.S. Provisional Patent Application No. 61,105,712, filed Oct. 15, 2008 (TRANSVI.026PR), the description of which is incorporated by reference herein in its entirety.

Figure 3:
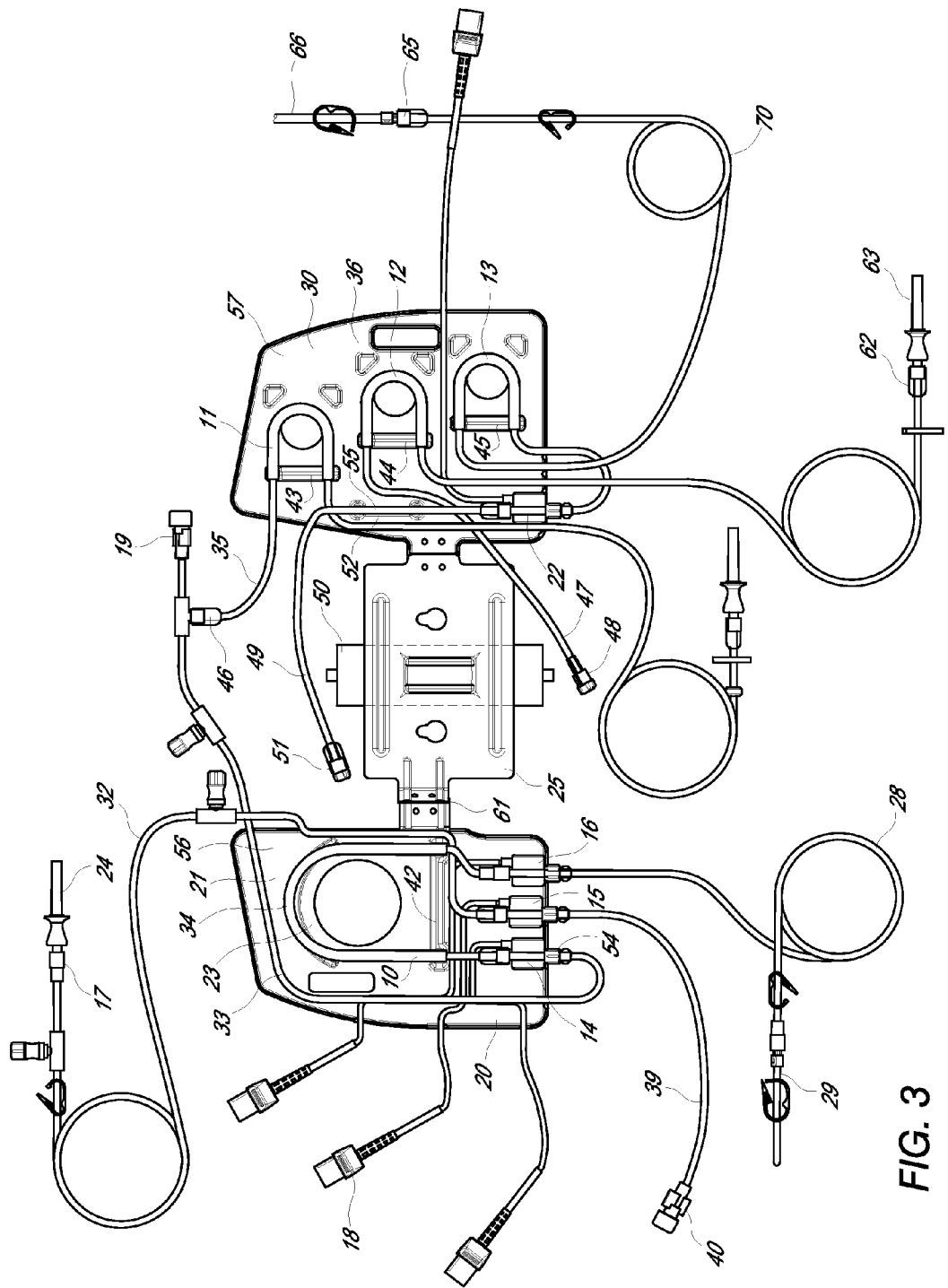
FIG. 3 shows the interior panel surfaces with mounted tubing on blood supply and fluid tubing panels and a connected center panel.

Referring to FIG. 3, there is shown the interior of the three panel set comprising the panel assembly described herein with the tubing mounted on or adjacent to the interior panel surface and portions of which tubing also extend beyond the panels to be connected to other tubing, cannulae for directing blood to and from a patient, as well as to fluid supply containers or an effluent container or bag.

A first panel 20, sometimes referred to herein as the "blood supply panel," has blood supply tubing 28 mounted in blood supply tube mounting space 21 defined interiorly of a generally continuous, normal side edge 41 which extends around the periphery of the interior panel surface 56.

Formed on the generally flat, planar interior panel surface and projecting therefrom is a blood tubing support member 42 which extends laterally across the interior panel surface and defining a blood pump space 23 around which is positioned an arched blood inlet tubing section 34. This arched tubing section is positioned and configured for engaging the rotor of a blood pump as will be explained further hereinafter. The panels are mounted generally vertically on the control unit housing, with the blood tubing support member 42 extending laterally across the interior panel surface, and blood pump space 23 is positioned above tubing support member 42. A space below tubing support member 42 allows for securing pressure transducers and blood tubing connections therein.

Figure 4:
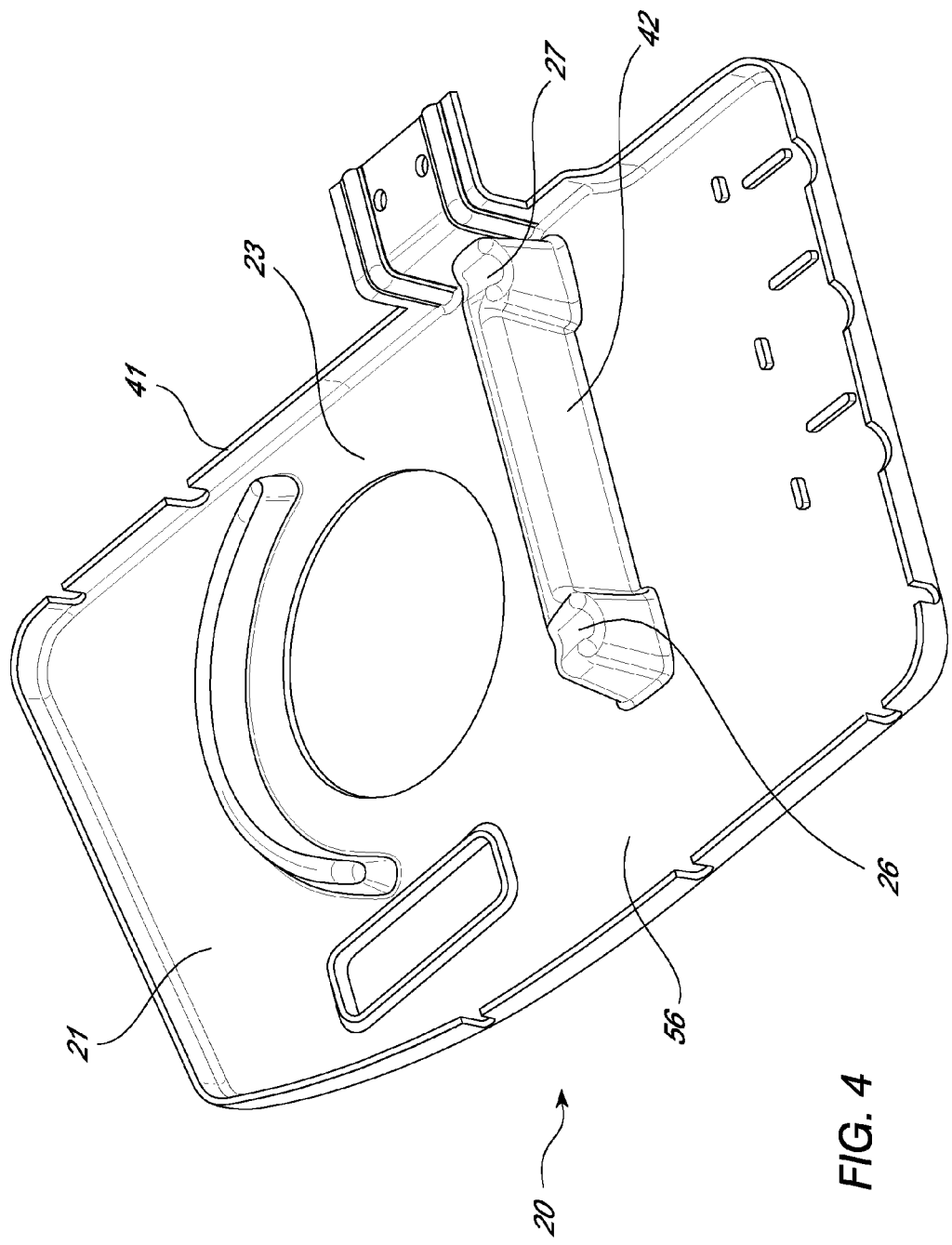
FIGS. 4 and 5 are perspective views of the interior surface of the blood and fluid supply tubing panels, respectively.

Referring further to FIGS. 3 and 4, the blood supply tubing directs blood from a patient via a patient access device such as a needle cannula 29 or a catheter and tubing 28 to the tubing section 34 mounted on the first panel 20. A portion of the tubing section 34 extends within the blood supply tube mounting space 21 between a first pressure transducer 14 and a second pressure transducer 16. The blood tubing section 34 is mounted in slanted channels 26 and 27 of the blood tubing support member 42, the channels being slanted upwardly toward the arch or U-shaped bend of the tubing section 34, thereby avoiding tubing droop and ensuring that the arched tubing section is and remains spaced from the interior panel surface and is presented for efficient engagement with the rotor of a blood pump when the panel is mounted on the hemofiltration assembly housing. The inclination or angle of the upwardly slanting tubing support channels is at least about 5° and preferably at least about 10° relative to the plane of the interior panel surface. The two opposite ends of the blood supply tubing section are secured to first and second pressure transducers 14 and 16, respectively.

A second blood supply tubing segment 33 extends along the interior surface of the first panel between the first pressure transducer 14 and passes through an opening or notch on the side edge 41 of the first panel terminating at an adapter 19 for being manually secured or disengaged from the inlet of a blood filter cartridge 50. It will be observed that a portion of the second blood inlet tubing segment 33 extends outside of the first panel 20 from its transducer tubing adapter 54 and then re-enters the tubing space of the panel.

Blood outlet tubing comprises two segments. Segment 32, one end of which is attached to third pressure transducer 15, extends along the interior panel surface and outwardly from the panel to an adapter 17 which is connected to a needle cannula 24 for returning treated blood to the patient. Another blood return tubing segment 39 has one end connected to third pressure transducer 15 and the other end to an adapter 40 for being manually secured or disengaged from an outlet of blood filter cartridge 50. Blood return tubing segment 39 is not secured along the interior of the first panel surface.

It is convenient to align and secure the three pressure transducers 14, 15 and 16 in the space along the interior first panel surface below the tubing support member 42, as illustrated in FIG. 3, although they may be positioned in other spaces. Moreover, the four pressure transducers (14, 15, 16, 22) are secured on the respective panels such that when the panels are mounted on the control unit housing, the pressure transducers are positioned at the same vertical height (elevation). Such a feature allows the pressures to be readily compared, without adjustment, which would otherwise be required to compensate for any difference in transducer heights.

Figure 5:
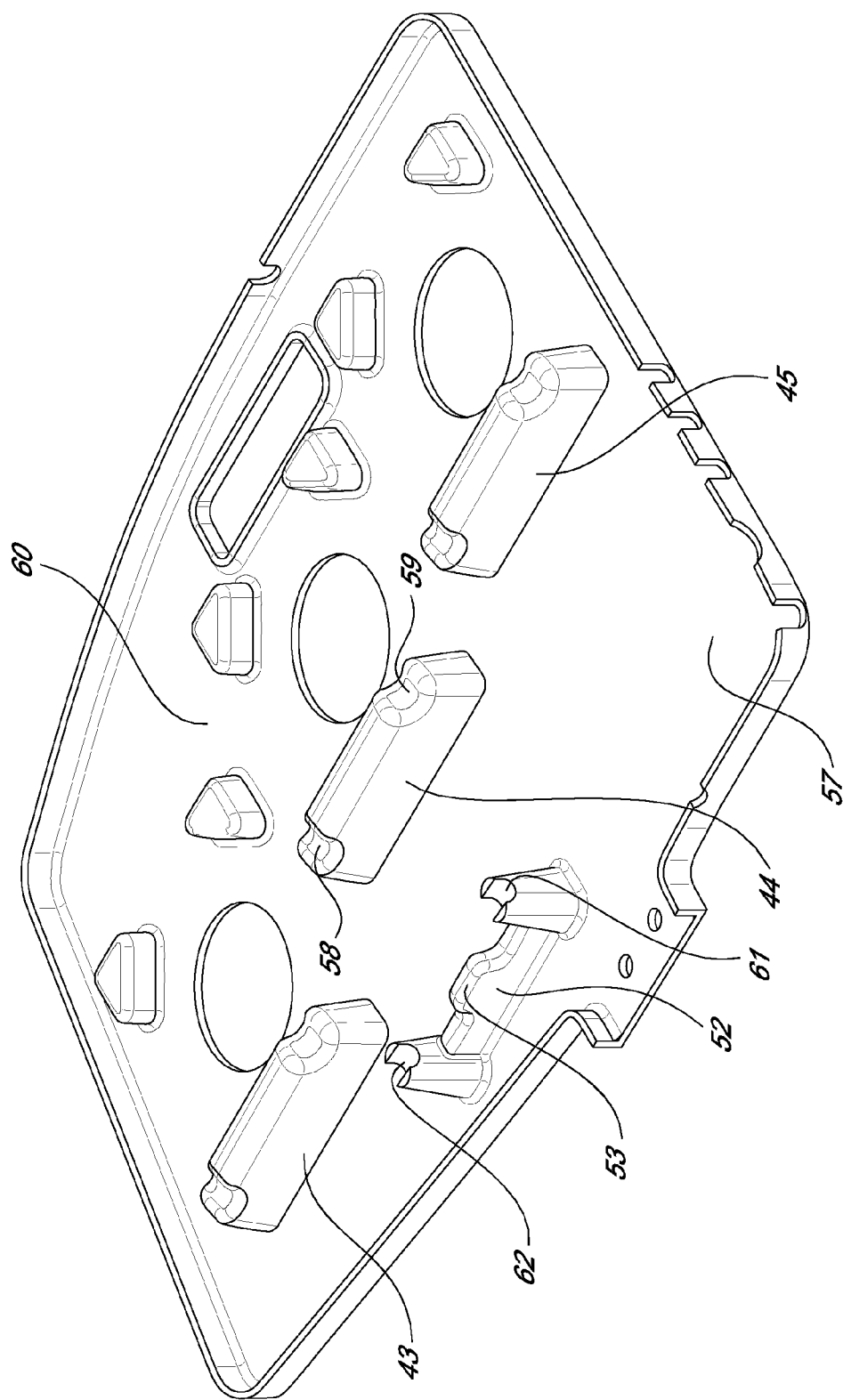

As shown in FIG. 3, second panel 30 comprises a generally flat, planar interior panel surface 57 defining a fluid supply tube mounting space 36 with fluid supply tubing secured along and adjacent to the panel surface. Like the first panel, the second panel also is provided with a generally continuous, normal side edge extending around the panel perimeter and defining the tube mounting space. The side edge is also preferably notched to provide slots for holding the tubing in place. The tube mounting space includes fluid pump space 60 for receiving a plurality of fluid pump rotors when the panel is mounted on the hemofiltration assembly housing. Observing also FIG. 5, a plurality of fluid tubing support members 43, 44, 45, each having a pair of slanted tubing support channels adjacent to opposite ends, are formed on and protrude from the flat interior panel surface 57. The fluid supply tubing comprises first tubing segment 35, second tubing segment 47 and third tubing segment 49, each characterized by an arched tubing section 11, 12, 13, respectively, and mounted in a different tubing support member. Tubing support channels 58, 59 in each support member are slanted upwardly toward the arched or U-shaped tubing sections at an angle of at least about 5° and preferably about 10° or more from the plane of the flat interior panel surface. Such a feature, as previously described regarding the arched tubing section 34 of the blood supply tubing, avoids arch-shaped tubing droop whereby the tubing is positioned to be efficiently and readily engaged by rotors of the respective fluid pumps when the panel is mounted on the hemofiltration assembly housing.

A portion of the first, second and third fluid supply tubing segments are secured along and adjacent to the interior panel surface. One end of first fluid supply tubing segment 35 terminates at an adapter 46 attached to second blood inlet tubing segment 33 upstream of the inlet of blood filter cartridge 50. The opposite end of the first fluid supply tubing segment 35 is attached to an adapter 67 and nozzle 68 cooperating with a replacement fluid container and/or source of saline and/or anticoagulant (not shown). The fluid pump which engages arched tubing section 11 of the first fluid supply tubing segment 35 pumps replacement fluid and/or saline and/or anticoagulant to blood in the tubing segment 33 upstream of the filter cartridge 50.

Second fluid supply tubing segment 47 and its arched section 12 extends between an adapter 48 attached to a dialysate fluid inlet on blood filter cartridge 50 and an adapter 62 and nozzle 63 for directing dialysate fluid from a dialysate fluid container or source (not shown). Third fluid supply tubing segment 49 extends between an adapter 51 for being secured to a dialysate effluent outlet on blood filter cartridge 50 and an opposite end 65 and nozzle 66 for directing the effluent to a container (not shown). Third fluid supply tubing segment 49 also passes through or is attached to a fourth pressure transducer 22 mounted on the second panel.

A portion 55 of third fluid supply tubing segment 49 is secured on a tubing bridge 52. Tube portion 55 is engaged in a slot of a blood detector when the second panel is mounted on the hemofiltration assembly housing. Such a blood detector, known to those skilled in the art, is mounted on the hemofiltration assembly housing to detect the presence of any blood in effluent passing through the tubing. In FIG. 2 a portion of blood detector 37 may be observed, as is the location of tubing bridge 52 on panel 30. Observing also FIG. 5, tubing bridge 52 is provided with a flange tube support 53 in the center of the bridge between tube receiving channels 61 and 62 at opposite ends of the bridge. These tube receiving channels are substantially aligned along a single axis for receiving and positioning tube portion 55 along the axis. Tube portion 55 will be positioned in an axial tube receiving slot in the blood detector when the second panel is mounted on the hemofiltration assembly housing. The blood detector slot is aligned along a single axis, preferably vertically, and thus it is important that tube portion 55 is also aligned along the same slot axis as it passes through the blood detector. The tubing bridge maintains the proper axial orientation of tube portion 55 for its installation and routing through the blood detector Although not previously described, the blood outlet tubing 32 also extends through an air detector and a return line clamp before it exits the control apparatus housing. Observing FIGS. 1 and 3, the portion of blood outlet tubing 32 extending away from the blood supply panel 20 is directed through air detector 72 and return line clamp 74 along the side of the apparatus housing.

In one embodiment, the tubing of the arched tubing sections, both blood and fluid tubing, are of a larger inside and outside diameter than the tubing that is secured along the inside surface of the two panels. For example, the inside diameter (ID) of the arched tubing segments may be of the same diameter as the outside diameter (OD) of the tubing to which the arched tubing sections are connected. In this regard, it may be convenient to simply insert and secure the ends of the smaller diameter tubing sections into the ends of the larger arched tubing sections. The larger diameter arched tubing sections may also be provided with thicker tubing walls giving more strength for engaging the rotors of the pumps.

A third panel 25 is positioned between and attached to the first and second panels. Hinges 61, for example living hinges, are used for attaching the blood and fluid panels to the third center panel. The third panel is configured to support a blood filter cartridge. A preferable means or component for supporting such a cartridge is an adjustable strap (not shown) which may be secured to slots in the panel and tightened around a filter cartridge on the face of the panel. Such an adjustable strap provides for releasably securing the filter cartridge so that an operator may mount a cartridge or change a cartridge readily, when desired.

The tubing may be secured along the panel surface and in the slots, recesses or channels as described using clips, brackets, hangers and the like. The tubing may be secured using a suitable adhesive, a UV curable adhesive or an ultrasonic weld.

What is claimed is:

1. A panel assembly configured for manually mounting on an extracorporeal blood therapy apparatus having a blood pump on a first side thereof and a plurality of fluid pumps on a second side thereof, said panel assembly characterized by:
a first panel comprising an interior panel surface defining a blood pump space and a blood supply tube mounting space having blood supply tubing secured along and adjacent to the interior panel surface, one or more blood tubing support members comprising tubing support channels adjacent to opposite ends thereof, said one or more blood tubing support members formed on and protruding from the interior panel surface adjacent to said blood pump space, and a plurality of pressure transducers mounted in said blood supply tube mounting space, wherein said blood supply tubing includes a length of first tubing comprising a first outside diameter and lengths of second tubing comprising a second outside diameter, smaller than said first outside diameter, and said blood supply tubing further comprises a first blood inlet tubing segment extending within said blood supply tube mounting space between a first pressure transducer and a second pressure transducer, a second blood inlet tubing segment having at least a portion thereof extending along the interior surface of said first panel between said first pressure transducer to a side edge of said panel, a blood outlet tubing segment having at least a portion thereof extending along the first panel interior surface between a third pressure transducer and a side edge of said panel, and wherein said first blood inlet tubing segment comprises an arched tubing section mounted in said opposite tubing support channels of said blood tube support member and extending therebetween into said blood pump space;
a second panel comprising an interior panel surface defining a fluid supply tube mounting space having fluid supply tubing secured along and adjacent to the interior panel surface, said fluid supply tube mounting space including fluid pump space and a plurality of fluid tubing support members comprising tubing support channels adjacent to opposite ends thereof, said fluid tubing support members formed on and protruding from the interior panel surface, wherein said fluid supply tubing comprises first, second and third fluid supply tubing segments, each segment comprising an arched tubing section mounted in said opposite tubing support channels of a different one of said fluid tubing support members and extending therebetween into said fluid pump space; and
a third panel flexibly connected to said first panel and said second panel and extending therebetween and configured to support a blood filter cartridge.

2. A panel assembly of claim 1 wherein said tubing support channels are slanted upwardly in the direction of the curve of the arched tubing sections, respectively.

3. A panel assembly of claim 1 wherein said first blood supply tubing segment comprises said first tubing, and said second and third blood supply tubing segments comprise said second tubing.

4. A panel assembly configured for manually mounting on an extracorporeal blood therapy apparatus having a blood pump on a first side thereof and a plurality of fluid pumps on a second side thereof, said panel assembly characterized by:
a first panel comprising an interior panel surface defining a blood pump space and a blood supply tube mounting space having blood supply tubing secured along and adjacent to the interior panel surface, one or more blood tubing support members comprising tubing support channels adjacent to opposite ends thereof, said one or more blood tubing support members formed on and protruding from the interior panel surface adjacent to said blood pump space, and a plurality of pressure transducers mounted in said blood supply tube mounting space, wherein said blood supply tubing comprises a first blood inlet tubing segment extending within said blood supply tube mounting space between a first pressure transducer and a second pressure transducer, a second blood inlet tubing segment having at least a portion thereof extending along the interior surface of said first panel between said first pressure transducer to a side edge of said panel, a blood outlet tubing segment having at least a portion thereof extending along the first panel interior surface between a third pressure transducer and a side edge of said panel, and wherein said first blood inlet tubing segment comprises an arched tubing section mounted in said opposite tubing support channels of said blood tube support member and extending therebetween into said blood pump space;
a second panel comprising an interior panel surface defining a fluid supply tube mounting space having fluid supply tubing secured along and adjacent to the interior panel surface, said fluid supply tube mounting space including fluid pump space and a plurality of fluid tubing support members comprising tubing support channels adjacent to opposite ends thereof, said fluid tubing support members formed on and protruding from the interior panel surface, wherein said fluid supply tubing comprises lengths of first tubing comprising a first outside diameter and lengths of second tubing comprising a second outside diameter, smaller than said first outside diameter, and fluid supply tubing further comprises first, second and third fluid supply tubing segments, each segment comprising an arched tubing section mounted in said opposite tubing support channels of a different one of said fluid tubing support members and extending therebetween into said fluid pump space; and
a third panel flexibly connected to said first panel and said second panel and extending therebetween and configured to support a blood filter cartridge.

5. A panel assembly of claim 1 wherein said first, second and third fluid supply tubing segments include fluid tubing sections extending along the second panel interior surface from a side edge thereof to an arched tube section.

6. A panel assembly of claim 1 wherein each said first, second and third fluid supply tubing segments comprise two fluid tubing sections extending from a side edge of the second panel to an arched tube section.

7. A panel assembly configured for manually mounting on an extracorporeal blood therapy apparatus having a blood pump on a first side thereof and a plurality of fluid pumps on a second side thereof, said panel assembly characterized by:
a first panel comprising an interior panel surface defining a blood pump space and a blood supply tube mounting space having blood supply tubing secured along and adjacent to the interior panel surface, one or more blood tubing support members comprising tubing support channels adjacent to opposite ends thereof, said one or more blood tubing support members formed on and protruding from the interior panel surface adjacent to said blood pump space, and a plurality of pressure transducers mounted in said blood supply tube mounting space, wherein said blood supply tubing comprises a first blood inlet tubing segment extending within said blood supply tube mounting space between a first pressure transducer and a second pressure transducer, a second blood inlet tubing segment having at least a portion thereof extending along the interior surface of said first panel between said first pressure transducer to a side edge of said panel, a blood outlet tubing segment having at least a portion thereof extending along the first panel interior surface between a third pressure transducer and a side edge of said panel, and wherein said first blood inlet tubing segment comprises an arched tubing section mounted in said opposite tubing support channels of said blood tube support member and extending therebetween into said blood pump space;

a second panel comprising an interior panel surface defining a fluid supply tube mounting space having fluid supply tubing secured along and adjacent to the interior panel surface, said fluid supply tube mounting space including fluid pump space and a plurality of fluid tubing support members comprising tubing support channels adjacent to opposite ends thereof, said fluid tubing support members formed on and protruding from the interior panel surface, wherein said fluid supply tubing comprises lengths of first tubing comprising a first outside diameter and lengths of second tubing comprising a second outside diameter, smaller than said first outside diameter, and fluid supply tubing further comprises first, second and third fluid supply tubing segments, each segment comprising an arched tubing section mounted in said opposite tubing support channels of a different one of said fluid tubing support members and extending therebetween into said fluid pump space, and each said first, second and third fluid supply tubing segments comprising two fluid tubing sections extending from a side edge of the second panel to an arched tube section; and a third panel flexibly connected to said first panel and said second panel and extending therebetween and configured to support a blood filter cartridge.

8. A panel assembly of claim 7 wherein said arched tubing sections of said fluid supply tubing segments comprise said first tubing and said fluid tubing sections comprise said second tubing.

9. A panel assembly of claim 8 wherein the outside diameter of the tubing of the arched tubing segment of said blood supply tubing is greater than the outside diameter of the tubing of the arched tubing segments of said fluid supply tubing.

10. A panel assembly of claim 1 including first, second and third pressure transducers secured on the first panel in said blood supply tube mounting space.

11. A panel assembly of claim 10 including a fourth pressure transducer secured on said second panel.

12. A panel assembly of claim 1 wherein said third panel is configured for removably securing a filter cartridge thereto.

13. A panel assembly of claim 1 wherein said first and second panels comprise generally flat, planar interior surfaces having a generally continuous normal side edge extending therearound.

14. A panel assembly of claim 1 wherein each of said first, second and third panels have one or more ports therethrough configured for removably engaging panel support members of a blood therapy apparatus.

15. A panel assembly of claim 14 including first, second and third pressure transducers secured on the first panel and a fourth pressure transducer secured on the second panel, and wherein said pressure transducers are secured on the respective panels such that they are positioned at substantially the same vertical height on the blood therapy apparatus.

16. A panel assembly of claim 14 wherein said first and second panel members have pump observation ports therethrough.

17. A panel assembly of claim 1 wherein said first panel has a blood pump observation port therethrough into said blood pump space.

18. A panel assembly of claim 1 wherein said second panel has three fluid pump observation ports therethrough.

19. A panel assembly of claim 17 wherein said second panel has three fluid pump observation ports therethrough.

20. A panel assembly of claim 19 wherein each of said first, second and third panels have one or more ports therethrough configured for removably engaging panel support members of a blood therapy apparatus.

21. A panel assembly of claim 10 wherein opposite ends of said first blood inlet tubing segment are secured to said first pressure transducer and said second pressure transducer, respectively.

22. A panel assembly of claim 21 wherein an end of said second blood inlet tubing segment is secured to said first pressure transducer.

23. A panel assembly of claim 11 wherein each of said pressure transducers comprises one or more adapters for releasably securing ends of tubing thereto.

24. A panel assembly of claim 10 wherein said first blood inlet tubing segment comprises a first end secured to said first pressure transducer and a second end secured to said second pressure transducer, wherein said second blood inlet tubing segment comprises a first end secured to said first pressure transducer and a second end having an adapter for being releasably secured to a blood filter cartridge inlet, and wherein said blood outlet tubing segment comprises a first end secured to said third pressure transducer and a second end having an adapter for being secured to a needle cannula assembly.

25. A panel assembly of claim 24 wherein said blood supply tubing further comprises a third blood inlet tubing segment comprising a first end having an adapter for being secured to a needle cannula assembly and a second end secured to said second pressure transducer.

26. A panel assembly of claim 25 wherein said blood supply tubing further comprises a blood return tubing segment comprising a first end having an adapter for being releasably secured to a blood filter cartridge outlet and a second end secured to said third pressure transducer.

27. A panel assembly of claim 1 wherein said first fluid supply tubing segment comprises a first end having an adapter for being releasably secured to said second blood inlet tubing and a second end for directing fluid from a saline or replacement fluid container, wherein said second fluid supply tubing segment comprises a first end having an adapter for being releasably secured to a blood filter cartridge and a second end for directing fluid from a dialysate fluid container, and wherein said third fluid supply tubing segment comprises a first end having an adapter for being releasably secured to a blood filter cartridge and a second end for directing hemofilter effluent to a container.

28. A panel assembly of claim 26 wherein said first fluid supply tubing segment comprises a first end having an adapter for being releasably secured to said second blood inlet tubing and a second end for directing fluid from a saline or replacement fluid container, wherein said second fluid supply tubing segment comprises a first end having an adapter for being releasably secured to a blood filter cartridge and a second end for directing fluid from a dialysate fluid container, and wherein said third fluid supply tubing segment comprises a first end having an adapter for being releasably secured to a blood filter cartridge and a second end for directing hemofilter effluent to a container.

29. A panel assembly of claim 28 including a fourth pressure transducer secured on said second panel and wherein said third fluid supply tubing is in fluid communication with said fourth pressure transducer.

30. A panel assembly of claim 1 further comprising a blood filter cartridge releasably mounted on said third panel.

31. A panel assembly of claim 24 further comprising a blood filter cartridge releasably mounted on said third panel.

32. A panel assembly of claim 26 further comprising a blood filter cartridge releasably mounted on said third panel.

33. A panel assembly of claim 28 further comprising a blood filter cartridge releasably mounted on said third panel.

34. A panel assembly configured for manually mounting on an extracorporeal blood therapy apparatus having a blood pump on a first side thereof and a plurality of fluid pumps on a second side thereof, said panel assembly characterized by:
   a first panel comprising an interior panel surface defining a blood pump space and a blood supply tube mounting space having blood supply tubing secured along and adjacent to the interior panel surface, one or more blood tubing support members comprising tubing support channels adjacent to opposite ends thereof, said one or more blood tubing support members formed on and protruding from the interior panel surface adjacent to said blood pump space, and a plurality of pressure transducers mounted in said blood supply tube mounting space, wherein said blood supply tubing comprises a first blood inlet tubing segment extending within said blood supply tube mounting space between a first pressure transducer and a second pressure transducer, a second blood inlet tubing segment having at least a portion thereof extending along the interior surface of said first panel between said first pressure transducer to a side edge of said panel, a blood outlet tubing segment having at least a portion thereof extending along the first panel interior surface between a third pressure transducer and a side edge of said panel, and wherein said first blood inlet tubing segment comprises an arched tubing section mounted in said opposite tubing support channels of said blood tube support member and extending therebetween into said blood pump space;
   a second panel comprising an interior panel surface defining a fluid supply tube mounting space having fluid supply tubing secured along and adjacent to the interior panel surface, said fluid supply tube mounting space including fluid pump space and a plurality of fluid tubing support members comprising tubing support channels adjacent to opposite ends thereof, said fluid tubing support members formed on and protruding from the interior panel surface, wherein said fluid supply tubing comprises first, second and third fluid supply tubing segments, each segment comprising an arched tubing section mounted in said opposite tubing support channels of a different one of said fluid tubing support members and extending therebetween into said fluid pump space;
   said first and second panels comprise generally flat, planar interior surfaces having a generally continuous normal side edge extending therearound, and said tubing support channels are slanted upwardly toward the arch of said tubing section at an angle of at least about 5° relative to the plane of said interior panel surface; and
   a third panel flexibly connected to said first panel and said second panel and extending therebetween and configured to support a blood filter cartridge.

35. A panel assembly configured for manually mounting on an extracorporeal blood therapy apparatus having a blood pump on a first side thereof and a plurality of fluid pumps on a second side thereof, said panel assembly characterized by:
   a first panel comprising an interior panel surface defining a blood pump space and a blood supply tube mounting space having blood supply tubing secured along and adjacent to the interior panel surface, one or more blood tubing support members comprising tubing support channels adjacent to opposite ends thereof, said one or more blood tubing support members formed on and protruding from the interior panel surface adjacent to said blood pump space, and a plurality of pressure transducers mounted in said blood supply tube mounting space, wherein said blood supply tubing comprises a first blood inlet tubing segment extending within said blood supply tube mounting space between a first pressure transducer and a second pressure transducer, a second blood inlet tubing segment having at least a portion thereof extending along the interior surface of said first panel between said first pressure transducer to a side edge of said panel, a blood outlet tubing segment having at least a portion thereof extending along the first panel interior surface between a third pressure transducer and a side edge of said panel, and wherein said first blood inlet tubing segment comprises an arched tubing section mounted in said opposite tubing support channels of said blood tube support member and extending therebetween into said blood pump space;
   a second panel comprising an interior panel surface defining a fluid supply tube mounting space having fluid supply tubing secured along and adjacent to the interior panel surface, said fluid supply tube mounting space including fluid pump space and a plurality of fluid tubing support members comprising tubing support channels adjacent to opposite ends thereof, said fluid tubing support members formed on and protruding from the interior panel surface, wherein said fluid supply tubing comprises first, second and third fluid supply tubing segments, each segment comprising an arched tubing section mounted in said opposite tubing support channels of a different one of said fluid tubing support members and extending therebetween into said fluid pump space;
   said first and second panels comprise generally flat, planar interior surfaces having a generally continuous normal side edge extending therearound, and said tubing support channels are slanted upwardly toward the arch of said tubing section at an angle of at least about 10° relative to the plane of said interior panel surface; and
   a third panel flexibly connected to said first panel and said second panel and extending therebetween and configured to support a blood filter cartridge.

36. A panel assembly of claim 1 wherein said third panel is connected to said first panel and said second panel with one or more living hinges, respectively.

37. A panel assembly of claim 1 wherein said third panel includes a component configured for releasably securing a filter cartridge thereon.

38. A panel assembly of claim 37 wherein said component comprises an adjustable strap.

39. A panel assembly of claim 1 wherein said second panel includes a fluid tubing bridge member formed and projecting from the interior panel surface and configured for supporting a length of fluid tubing in a substantially vertical orientation.

40. A panel assembly of claim 27 wherein said second panel includes a fluid tubing bridge member formed and projecting from the interior panel surface and configured for supporting a length of fluid tubing in a substantially vertical orientation, and wherein a portion of said third fluid supply tubing segment is secured to said bridge member and extends thereon between opposite ends of said bridge member.

41. A panel assembly of claim 40 wherein said bridge member comprises tube receiving channels at opposite ends thereof, said channels being substantially aligned along a single axis, and wherein said third fluid supply tubing segment is secured within said channels and extends therebetween along said single axis.

42. A panel assembly configured for manually mounting on an extracorporeal blood therapy apparatus having a blood pump on a first side thereof and a plurality of fluid pump on a second side thereof, said panel assembly characterized by:

a first panel comprising an interior panel surface defining a blood pump space and a blood supply tube mounting space having blood supply tubing secured along and adjacent to the interior panel surface, one or more blood tubing support members comprising tubing support channels adjacent to opposite ends thereof, said one or more blood tubing support members formed on and protruding from the interior panel surface adjacent to said blood pump space, and a plurality of pressure transducers mounted in said blood supply tube mounting space, wherein said blood supply tubing comprises a first blood inlet tubing segment extending within said blood supply tube mounting space between a first pressure transducer and a second pressure transducer, a second blood inlet tubing segment having at least a portion thereof extending along the interior surface of said first panel between said first pressure transducer to a side edge of said panel, a blood outlet tubing segment having at least a portion thereof extending along the first panel interior surface between a third pressure transducer and a side edge of said panel, and wherein said first blood inlet tubing segment comprises an arched tubing section mounted in said opposite tubing support channels of said blood tube support member and extending therebetween into said blood pump space;

a second panel comprising an interior panel surface defining a fluid supply tube mounting space having fluid supply tubing secured along and adjacent to the interior panel surface, said fluid supply tube mounting space including fluid pump space and a plurality of fluid tubing support members comprising tubing support channels adjacent to opposite ends thereof, said fluid tubing support members formed on and protruding from the interior panel surface, wherein said fluid supply tubing comprises first, second and third fluid supply tubing segments, each segment comprising an arched tubing section mounted in said opposite tubing support channels of a different one of said fluid tubing support members and extending therebetween into said fluid pump space, said first fluid supply tubing segment further comprises a first end having an adapter for being releasably secured to said second blood inlet tubing and a second end for directing fluid from a saline or replacement fluid container, wherein said second fluid supply tubing segment comprises a first end having an adapter for being releasably secured to a blood filter cartridge and a second end for directing fluid from a dialysate fluid container, and wherein said third fluid supply tubing segment comprises a first end having an adapter for being releasably secured to a blood filter cartridge and a second end for directing hemofilter effluent to a container, said second panel including a fluid tubing bridge member formed and projecting from the interior panel surface and configured for supporting a length of fluid tubing in a substantially vertical orientation, and wherein a portion of said third fluid supply tubing segment is secured to said bridge member and extends thereon between opposite ends of said bridge member, said bridge member comprising tube receiving channels at opposite ends thereof, said channels being substantially aligned along a single axis, and wherein said third fluid supply tubing segment is secured within said channels and extends therebetween along said single axis, and said bridge member further comprising at least one tube support flange positioned between said channels and configured to support said tubing segment extending between said channels along said single axis; and a third panel flexibly connected to said first panel and said second panel and extending therebetween and configured to support a blood filter cartridge.

* * * * *